United States Patent
Brandl et al.

(10) Patent No.: US 10,245,364 B2
(45) Date of Patent: Apr. 2, 2019

(54) SAFETY APPARATUS FOR EXTRACORPOREAL BLOOD TREATMENT

(71) Applicant: Fresenius Medical Care Deutschland GmbH, Bad Homburg (DE)

(72) Inventors: Martin Brandl, Spitz (AT); Dieter Falkenhagen, Krems (AT); Jens Hartmann, Furth (AT)

(73) Assignee: Fresenius Medical Care Deutschland GmbH (DE)

( * ) Notice: Subject to any disclaimer, the term of this patent is extended or adjusted under 35 U.S.C. 154(b) by 476 days.

(21) Appl. No.: 14/394,949

(22) PCT Filed: Apr. 15, 2013

(86) PCT No.: PCT/EP2013/057788
§ 371 (c)(1),
(2) Date: Oct. 16, 2014

(87) PCT Pub. No.: WO2013/156435
PCT Pub. Date: Oct. 24, 2013

(65) Prior Publication Data
US 2015/0122712 A1    May 7, 2015

(30) Foreign Application Priority Data
Apr. 16, 2012 (EP) .................... 12164284

(51) Int. Cl.
- *A61M 1/16* (2006.01)
- *A61M 1/36* (2006.01)
- *B01D 61/30* (2006.01)
- *B01D 61/32* (2006.01)

(52) U.S. Cl.
CPC ............ *A61M 1/1603* (2014.02); *A61M 1/16* (2013.01); *A61M 1/1609* (2014.02);
(Continued)

(58) Field of Classification Search
CPC .... A61M 1/16; A61M 1/1601; A61M 1/1603; A61M 1/1605; A61M 1/1607;
(Continued)

(56) References Cited

U.S. PATENT DOCUMENTS 4,451,454 A * 5/1984 Wong .................... A61K 33/00
424/422
4,668,400 A * 5/1987 Veech ................. A61M 1/1656
210/647

(Continued)

FOREIGN PATENT DOCUMENTS

CA    2173672 A2    2/1997
DE    10114283 C2   4/2003
(Continued)

OTHER PUBLICATIONS

International Search Report and Written Opinion for International Application No. PCT/EP2013/057788, Search completed Jul. 4, 2013, dated Jul. 17, 2013, 11 Pgs.

*Primary Examiner* — Joseph W Drodge
(74) *Attorney, Agent, or Firm* — KPPB LLP (57) ABSTRACT

Blood purification device having an extracorporeal blood circuit with a blood inflow and outflow to and from a dialysis unit, wherein the dialysis unit comprises a dialysis solution inflow and a dialysate outflow, characterized by a control loop for control of the acid-base equilibrium of the blood, wherein bicarbonate is supplied to the blood using an aqueous bicarbonate-containing solution, wherein a measuring means for measuring a blood buffer parameter is associated with the control loop, wherein the blood buffer parameter is selected from one of bicarbonate concentration and $CO_2$ partial pressure, and wherein a signal corresponding to the measured value of the blood buffer parameter can be supplied to a closed-loop control apparatus, which regulates the value of the blood buffer parameter by the supply (Continued)

of bicarbonate, and at least one pH-measuring means, wherein a signal corresponding to the pH value can be supplied to an alarm apparatus.

6 Claims, 4 Drawing Sheets

(52) U.S. Cl.
CPC .......... *A61M 1/361* (2014.02); *A61M 1/3612* (2014.02); *A61M 1/3621* (2013.01); *A61M 1/3672* (2013.01); *A61M 1/3675* (2013.01); *B01D 61/30* (2013.01); *B01D 61/32* (2013.01); *A61M 2205/18* (2013.01); *A61M 2205/3324* (2013.01); *A61M 2230/202* (2013.01); *A61M 2230/208* (2013.01); *F04C 2270/0421* (2013.01)

(58) Field of Classification Search
CPC .... A61M 1/1609; A61M 1/1654; A61M 1/36; A61M 1/361; A61M 1/3607; A61M 1/3621; A61M 1/3672; A61M 2205/3324; A61M 2230/02; A61M 2230/20; A61M 2230/208; B01D 61/30; B01D 61/32
USPC .... 210/646, 647, 96.2; 604/4.01, 5.01, 6.01, 604/29, 65, 67
See application file for complete search history.

(56) References Cited

U.S. PATENT DOCUMENTS

| | | | | |
|---|---|---|---|---|
| 5,744,031 | A * | 4/1998 | Bene | A61M 1/16 210/143 |
| 6,156,007 | A * | 12/2000 | Ash | A61M 1/3679 604/113 |
| 2002/0077579 | A1* | 6/2002 | Tobe | A61K 33/06 604/5.01 |
| 2003/0010701 | A1* | 1/2003 | Collins | A61M 1/3413 210/321.6 |
| 2004/0133145 | A1 | 7/2004 | Bene et al. | |
| 2007/0066928 | A1 | 3/2007 | Lannoy | |
| 2008/0015487 | A1* | 1/2008 | Szamosfalvi | A61M 1/3672 604/6.07 |
| 2009/0027095 | A1 | 1/2009 | Matsui | |
| 2009/0131769 | A1* | 5/2009 | Leach | A61B 5/0031 600/309 |
| 2011/0142700 | A1* | 6/2011 | Gura | A61M 1/1696 417/474 |
| 2011/0208105 | A1* | 8/2011 | Brandl | A61M 1/342 604/5.01 |
| 2012/0273420 | A1* | 11/2012 | Gerber | A61B 5/0031 210/647 |
| 2012/0277650 | A1* | 11/2012 | Gerber | A61B 5/0031 604/5.01 |

FOREIGN PATENT DOCUMENTS

| | | |
|---|---|---|
| DE | 102009018649 A1 | 10/2010 |
| EP | 0097366 A2 | 1/1984 |
| EP | 0759551 A2 | 2/1997 |
| EP | 1110562 A2 | 6/2001 |
| WO | 9106326 A1 | 5/1991 |
| WO | 2009026603 A1 | 3/2009 |
| WO | 2012038384 A1 | 3/2012 |

* cited by examiner

SAFETY APPARATUS FOR EXTRACORPOREAL BLOOD TREATMENT

The invention generally relates to a blood purification device having an extracorporeal blood circuit with a blood inflow to a dialysis unit for blood removal from a patient and a blood outflow from the dialysis unit for blood being guided back into the patient, wherein the dialysis unit comprises an inflow for a dialysis solution and a dialysate outflow.

The mammal organism only functions perfectly when the same physical and chemical conditions prevail where possible. The maintenance of the acid-base equilibrium, which is kept constant within a very narrow physiological range by mechanisms occurring naturally in the body, is particularly important. The carbonic acid-bicarbonate buffer system forms the majority of the total buffer capacity of blood and plays a key role when balancing pH fluctuations of the blood. Acid metabolites, which form constantly in the body, are usually neutralised by being either discharged via the kidneys or exhaled via lung $CO_2$. In humans, the pH value of blood lies in a very narrow range between 7.35-7.45. If the pH value is below 7.35, reference is made to acidosis, and if it lies above 7.45 reference is then made to alkalosis. Both acidosis and alkalosis are dangerous disturbances of the acid-base equilibrium, which, besides significant physical complaints (for example headaches, muscles cramps, bone damage, nausea and fatigue), may also lead to acutely life-threatening states.

In patients with chronic kidney failure and dialysis patients, these acid metabolites can no longer be discharged sufficiently via the kidneys. The lacking kidney function can only be balanced to a limited extent by the lungs. The overacidification of the blood by unremoved acid metabolites therefore leads, in dialysis patients, to metabolic acidosis, which is characterised by a decrease of the pH value of the blood and of the bicarbonate concentration in the blood. During extracorporeal blood purification, the blood of a patient therefore is not only purified of harmful substances, but the occurred overacidification of the blood is also balanced.

Earlier, acetate was used for acidosis correction and is converted in the human body to form the alkaline buffer bicarbonate. Since this conversion of the acetate in the body leads to a delayed effect, acidosis is nowadays counteracted as standard using bicarbonate (bicarbonation, $HCO_3^-$), which is fed to the blood following filtration, either at the membrane interface of the dialysis filter by means of a bicarbonate-containing dialysis fluid (in the case of haemodialysis and haemodiafiltration) or by means of a bicarbonate-containing infusion solution (in the case of haemodiafiltration and haemofiltration). The bicarbonate reacts with the (acidic) $H^+$ ions in the blood to form carbonic acid, which in turn dissociates to form $H_2O$ (water) and $CO_2$ (carbon dioxide):

$$CO_2 + H_2O \Longleftrightarrow H_2CO_3 \Longleftrightarrow H^+ + HCO_3^-$$

The carbon dioxide is exhaled via the lungs and the water is removed via the dialysis or via filtration. Dialysis is nowadays performed primarily as bicarbonate dialysis. A mixture of bicarbonate and acetate is often also used, wherein the dialysate is mixed together immediately prior to the passage through a dialyser (dialysis filter) from a concentrated acetate solution (acidic components) and a concentrated bicarbonate solution (alkaline component) and water.

To start extracorporeal blood purification, which may be based on the principle of haemodialysis, haemofiltration or haemodiafiltration, the degree of acidity in the blood is usually determined by means of blood gas analysis and the bicarbonate feed is set on the basis of the value obtained. An excessive correction of the acid-base balance toward the alkaline range may in turn pose a risk for the patient. A bicarbonate dialysis is used practically exclusively in the case of acute dialysis and in the case of chronic haemodialysis.

Disturbances of the acid-base balance and fluctuations of the blood pH value constitute a high safety and health risk for a dialysis patient and may lead to life-threatening states. It is therefore desirable to recover the constancy of the pH value of the blood or to maintain the acid-base balance.

The object of many embodiments of the invention is therefore to provide measures that counteract a disturbance of the acid-base balance and keep constant the blood pH value in order to recover and to maintain the wellbeing of the patient on the one hand and to prevent the occurrence of dangerous physiological states on the other hand. In particular, the object of several embodiments of the invention is to prevent the occurrence of acidosis or alkalosis, of which the effects not only present a high level of stress for the organism, but may also be life-threatening.

The object is achieved by a blood purification device as mentioned in the introduction, which, in accordance with many embodiments of the invention, is characterised by a control loop for controlling the acid-base balance of the blood, wherein bicarbonate is supplied to the blood by means of an aqueous bicarbonate-containing solution, wherein at least one measuring means for measuring a blood buffer parameter is associated with the control loop, wherein the blood buffer parameter is selected from the group consisting of bicarbonate concentration and $CO_2$ partial pressure, and wherein a signal corresponding to the measured actual value of the blood buffer parameter can be supplied to a control apparatus, which regulates the actual value of the blood buffer parameter via the supply of the bicarbonate to a predeterminable intended value or intended value range, and wherein the blood purification device is further characterised by at least one pH-measuring means, which is arranged upstream of the dialysis unit in the extracorporeal blood circuit, wherein a signal corresponding to the pH value can be supplied to an alarm apparatus, which triggers an alarm signal if a predeterminable pH value or pH-value range is exceeded or undershot.

In many embodiments of the invention, a control is provided with extracorporeal blood purification, by means of which control disturbances to the acid-base balance, such as acidosis or alkalosis, are prevented and the maintenance of the physiological pH value of the blood and therefore of the acid-base balance is ensured. In a number of embodiments, it is also possible to immediately identify disturbances of the acid-base balance and to counteract these disturbances, such that the risk of serious or even life-threatening states can be kept as low as possible. Numerous embodiments of the invention thus contribute to a significant improvement of patient safety.

The specific combination according to a number of embodiments of the invention of a control loop comprising a measuring means for measuring a blood buffer parameter and a pH-measuring means arranged upstream of the dialysis unit enables the distinction between a compensated and a non-compensated alkalosis and/or acidosis. A non-compensated alkalosis and/or acidosis then occurs whenever there is a shift from the physiological pH value, that is to say when a pH of 7.45 is exceeded or a pH of 7.35 is undershot. In the case of a non-compensated alkalosis or acidosis, this poses a great risk for the patient. Analogously, in the case of a compensated alkalosis or a compensated acidosis, the blood buffer parameter (that is to say the bicarbonate concentration or $CO_2$ partial pressure) deviates from the normal range, whereas the pH value is in the normal range. In the case of a non-compensated alkalosis or a non-compensated acidosis, both the blood buffer parameter (that is to say the bicarbonate concentration or the $CO_2$ partial pressure) and the pH value are outside the corresponding normal ranges. A pH value measured upstream of the dialysis unit corresponds to the current intracorporeal pH value of the patient blood and enables a rapid identification of a non-compensated alkalosis or acidosis.

EP0097366 describes a dialysis device with controlled electrolyte composition of the dialysis solution, wherein detectors are provided for measuring the electrolytes present in the blood, conductivity or pH value. The features of the present invention including the associated advantages in terms of patient safety are neither disclosed therein nor considered in any form.

The $HCO_3^-$ concentration (bicarbonate concentration) and the $CO_2$ partial pressure ($pCO_2$) are blood buffer parameters that are used conventionally in clinical application to assess the acid-base equilibrium of a mammal, in particular humans. The term acid-base balance is used synonymously with the term acid-base equilibrium. The origin and the manifestation of alkalosis or acidosis can be determined on the basis of the two aforementioned blood buffer parameters. Metabolic disturbances can be detected characteristically on the basis of the deviations in the $HCO_3^-$ concentration in the blood and can be assessed in terms of severity. The pH value, the $HCO_3^-$ concentration and the $CO_2$ partial pressure are interlinked via the Henderson-Hasselbalch equation.

Due to the compensation mechanisms taking place in the body, an almost normal pH value does not rule out the presence of an acid-base imbalance. The measuring means for measuring a blood buffer parameter is provided in order to measure the $HCO_3^-$ concentration or the $CO_2$ partial pressure for the assessment of the acid-base balance. In many embodiments of the present invention, the current $HCO_3^-$ concentration or the $CO_2$ partial pressure in the blood is measured constantly, and the actual value is controlled to a predeterminable intended value or intended range by the supply of the aqueous bicarbonate solution.

The normal values of the $HCO_3^-$ concentration typically lie at 21-26 mmol/l and the normal values of the $CO_2$ partial pressure lie typically at 35-45 mm Hg. The predeterminable intended value or intended range consequently corresponds typically to these normal values. Depending on the state of the patient, the intended range may also be predetermined so as to be narrower than the previously mentioned respective typical normal range.

In order to make an operator aware of the state of a non-compensated alkalosis or a non-compensated acidosis, in accordance with many embodiments of the invention an alarm signal is triggered by the alarm apparatus if a predeterminable pH value or pH-value range is exceeded or undershot. By way of example, the alarm signal may be an acoustic or optical signal. Due to the signal, an operator can take suitable countermeasures immediately. In addition, the triggering of an alarm may result in a discontinuation of the blood purification unit and therefore of the blood purification process.

Alarm apparatuses and control apparatuses as can be used with this invention have long been known to a person skilled in the art of extracorporeal blood purification units. The alarm apparatus and the control apparatus are typically associated with the central unit electronics and control system, but may also be completely independent electronic components.

pH-measuring means for measuring the blood pH value during an extracorporeal blood purification are known to a person skilled in the relevant art. A pH-measuring means suitable for use in the present invention is, for example, a pH sensor produced by the company Lazar Research Laboratories, Inc., for example a pH sensor of the FTPH-2SXS type.

Suitable measuring means for measuring a blood buffer parameter, which can be used in this invention, are also described in the prior art. By way of example, sensors for measuring the $HCO_3^-$ concentration and/or the $CO_2$ partial pressure are disclosed in EP 0759 551 B1, CA 2173672 A2 and US 2009/027095 A1 and are suitable for carrying out this invention. These sensors are also suitable for the continuous measurement of the blood buffer parameters of the blood circulating in the extracorporeal blood circuit. In certain embodiments, the measuring means can be inserted into the extracorporeal blood circuit and the measuring means is in contact with the blood flowing past. In these cases, high demands are placed on the quality of the measuring means in terms of sterility and biocompatibility. Alternatively, in other embodiments, a small quantity of blood can be conveyed via a bypass line from the extracorporeal blood circuit to a measuring means and then discarded.

The expression "at least one measuring means" is understood within the scope of this disclosure to mean that only one measuring means for measuring the pH value or blood buffer parameter or also more than one measuring means, for example two or more similar measuring means, which measure alternately or simultaneously, is/are arranged at a certain position.

The term "continuous measurement" is to be understood in the context of the instant application to mean a measurement of the blood buffer parameter or of the pH value at regular intervals, wherein the intervals are advantageously kept sufficiently short in order to monitor the acid-base equilibrium sufficiently closely. Sufficiently short intervals are those with which it can be ensured that a development in the direction of an unphysiological state of the patient can be identified in good time and counteracted. With most applications, an interval from 30 to 60 minutes is sufficient. In some patient groups, for example patients with liver diseases, which can convert the citrate supplied in the case of citrate anticoagulation into bicarbonate only to a limited extent (see further below), the interval between two successive measurements is selected so as to be shorter, for example 15 minutes.

The term "extracorporeal blood purification" includes various blood purification methods on membrane basis, such as haemodialysis, (what is known as online) haemofiltration and (what is known as online) haemodiafiltration as well as a combination of these methods with methods based on absorption, such as haemoperfusion, plasmasorption, etc., wherein all of these methods are known to a person skilled in the relevant art.

The acid-base balance is controlled via the supply of bicarbonate ($HCO_3^-$) by means of a bicarbonate-containing aqueous solution, since this, as mentioned above, also constitutes a key alkaline component of the blood buffer system occurring naturally in the body and constitutes an agent that has long been proven and approved in clinical use.

In a first advantageous embodiment, the aqueous bicarbonate solution is a dialysis solution that is conveyed into the dialysis unit (also referred to as a dialyser or dialysis filter) via the inflow for dialysis solution. This embodiment is expedient in particular for haemodialysis and haemodiafiltration. Bicarbonate is supplied to the blood via the dialysis fluid (bicarbonate dialysis). Bicarbonate dialysis is known per se to a person skilled in the relevant art. The composition of the dialysis solution is expediently modified by the control loop according to many embodiments of the invention. In a conventional embodiment known to a person skilled in the relevant art, the dialysis solution is mixed together, prior to the passage through the dialyser, from a concentrated acidic component (for example acetate solution) and a concentrated alkaline component (bicarbonate solution) and the rest of the components of the dialysis solution. By increasing or reducing the admixed quantity of bicarbonate, the concentration of bicarbonate in the dialysis solution can be varied accordingly.

In a further advantageous embodiment. The aqueous bicarbonate solution, by means of which bicarbonate is supplied to the blood, is an infusion solution. This embodiment is expedient in particular for haemofiltration, haemodiafiltration and online haemodiafiltration. Here, the bicarbonate can be supplied to the blood by means of a substitution solution (also referred to as substitution medium or substitute), preferably by means of infusion into the extracorporeal blood circuit.

The bicarbonate is added via a mixing system to the dialysate or the substitute shortly before the filter, preferably in a ratio from 1:28 to 1:32. Mixing systems of this type are known to a person skilled in the art. Since the bicarbonate is admixed shortly before passing through the filter, a precipitation of unsolvable carbonate compounds is prevented.

In most patients requiring extracorporeal blood purification, an inhibition of the blood coagulation is necessary. Heparin is used as the current standard in clinical treatment. An alternative to the Heparin method is constituted by anticoagulation using citrate. In one embodiment, the blood purification device therefore comprises a citrate anticoagulation apparatus, wherein citrate is supplied to the extracorporeal blood circuit at a citrate supply point upstream of the dialysis unit and substitution medium is supplied at a substitution medium supply point downstream of the dialysis unit.

In the case of anticoagulation with citrate, disturbances in the acid-base equilibrium may occur particularly easily. With this form of anticoagulation, citrate is supplied to the blood constantly and is converted in the body into bicarbonate and can lead to unphysiological blood pH values, which constitute a real risk for the patient. Due to an accumulation of bicarbonate in the organism of the patient, alkalosis may occur to a life-threatening extent. Acidosis is also possible, which then in particular occurs when a non-functioning liver, for example in the case of patients with liver insufficiency or liver failure, is unable to convert the citrate sufficiently into bicarbonate, whereby the citrate remains in the blood. Many embodiments of the invention are therefore particularly advantageous when the blood is anticoagulated using citrate and makes it possible to recover the constancy of the pH value of the blood or to maintain the acid-base balance.

Dialysis methods using citrate anticoagulation are known from the prior art, for example from WO 91/06326, US 2007/066928 A1, US 2004/133145A1, DE 101 14 283 C2 and WO 2009/026603. With a blood purification device according to numerous embodiments of the invention, which are equipped with a citrate anticoagulation apparatus, the bicarbonate-containing solution may be either the dialysis solution or the substitution medium.

If a citrate anticoagulation apparatus is associated with the blood purification device, the at least one pH-measuring means is then preferably arranged in the extracorporeal blood circuit upstream of the citrate supply point. The pH value measured at this position corresponds to the currently intracorporeally present pH value of the patient blood and enables a rapid countermeasure in the case of an unphysiological pH value.

In an advantageous embodiment of the invention, the at least one measuring means for measuring a blood buffer parameter is arranged in the extracorporeal blood circuit upstream of the dialysis unit. The value of the blood buffer parameter measured at this position reflects the currently intracorporeally present acid-base balance and enables a rapid countermeasure in the case of a disturbance of the acid-base balance.

If a citrate anticoagulation apparatus is associated with the blood purification device, it is then expedient when the at least one measuring means for measuring a blood buffer parameter is arranged in the extracorporeal blood circuit upstream of the citrate supply point. The advantage of this arrangement lies in the fact that a measurement of the blood buffer parameter performed upstream of the citrate supply point in the extracorporeal blood steam represents the currently intracorporeally present acid-base balance, which is modified following addition of citrate. An insufficient conversion of the citrate into bicarbonate in the liver of the patient and the associated risk of alkalosis can be immediately identified and can be bypassed by means of the control mechanism according to some embodiments of the invention by reducing the bicarbonate supply. Bicarbonate ($HCO_3^-$) is supplied via the substitution medium in a sub-variant of this embodiment. Since the substitution medium in the case of citrate anticoagulation usually contains calcium ions, which may occasionally precipitate with the bicarbonate as calcium carbonate, the bicarbonate may alternatively also be infused in the form of an aqueous substitution solution into the extracorporeal blood circuit via further, separate access.

Alternatively to the above-mentioned embodiment, in which the measuring means for measuring a blood buffer parameter is arranged upstream of the dialysis unit or upstream of the citrate supply point, the at least one measuring means for measuring a blood buffer parameter is arranged in the dialysate outflow in a further advantageous embodiment. The arrangement in the dialysate outflow has the advantage that the measuring means does not come into direct contact with the blood and therefore, in contrast to a measuring means arranged on the blood side, no contamination whatsoever of the patient can occur, for example by means of germs or non-biocompatible measuring means materials. The clinical approval of the measuring means is thus simplified considerably. Furthermore, an adhesion of cells and proteins to the measuring means surface in the dialysate is ruled out, whereby the measuring means has good long-term stability.

As a development of the above-mentioned embodiments, in which at least one first blood buffer measuring means is arranged in a first position, at least one additional second measuring means for measuring a blood buffer parameter can be associated as a further safety measure with the control loop at a second position. The second additional measuring means is used either to identify malfunctions of the first measuring means functioning for control, or the second additional measuring means can also be incorporated into the control, similarly to the first measuring means.

In a first variant, with the presence of at least one first blood buffer parameter measuring means upstream of the dialysis filter or upstream of the citrate supply point, at least one second additional measuring means arranged in the dialysate outflow for measuring a blood buffer parameter is associated with the control loop. In a second variant, with the presence of at least one first blood buffer parameter measuring means in the dialysate outflow, at least one second additional measuring means for measuring a blood buffer parameter is associated with the control loop and is arranged in the extracorporeal blood circuit upstream of the dialysis unit. If a citrate anticoagulation apparatus is associated with the blood purification device, it is then expedient if the additional measuring means is arranged in the extracorporeal blood circuit upstream of the citrate supply point.

In addition, in a development of the previously mentioned embodiments, at least one additional measuring means for measuring a blood buffer parameter can be associated with the control loop and is arranged in the extracorporeal blood circuit downstream of the dialysis unit. If a citrate anticoagulation apparatus is associated with the blood purification device, it is then expedient if the additional measuring means in the extracorporeal blood circuit is arranged downstream of the dialysis unit and upstream of the substitution medium supply point. This at least one additional measuring means serves as an additional safety measure and can function either in order to identify malfunctions of the measuring means used for control or is incorporated into the control.

If may also be advantageous if the blood purification device comprises at least one additional pH-measuring means, which is arranged in the extracorporeal blood circuit downstream of the dialysis unit, wherein a signal corresponding to the pH value can be supplied to the alarm apparatus, which triggers an alarm signal if a predeterminable pH value or pH-value range is exceeded or undershot. If a citrate anticoagulation apparatus is associated with the blood purification device, it is then expedient when the at least one additional pH-measuring means is arranged in the extracorporeal blood circuit downstream of the substitution medium supply point. Due to this additional pH-measuring means downstream of the dialysis unit or downstream of the substitution medium supply point, the pH value of the blood circulating in the extracorporeal blood circuit is checked again, before the blood is supplied back again into the body. A pH measurement at these positions thus constitutes an additional safety measure. In particular, with provided citrate anticoagulation, an incorrect dosing of the substitution medium, which may lead to disturbances of the acid-base equilibrium and to pH value shifts, can be quickly identified in particular.

The above-described blood purification device in accordance with many embodiments of the invention, including the developments thereof, is used advantageously in order to prevent or to treat disturbances of the acid-base balance during an extracorporeal blood purification. Disturbances of the acid-base balance comprise acidosis and alkalosis. The extracorporeal blood purification device may be based on the principle of haemodialysis, haemofiltration and haemodiafiltration, as described further above, optionally in combination with adsorption technology. The extracorporeal blood purification is advantageously performed with anticoagulation using citrate, in which case the blood purification device according to numerous embodiments of the invention demonstrates particularly advantageous effects in respect of patient safety and the restoration or safeguarding of wellbeing.

Figure 1:
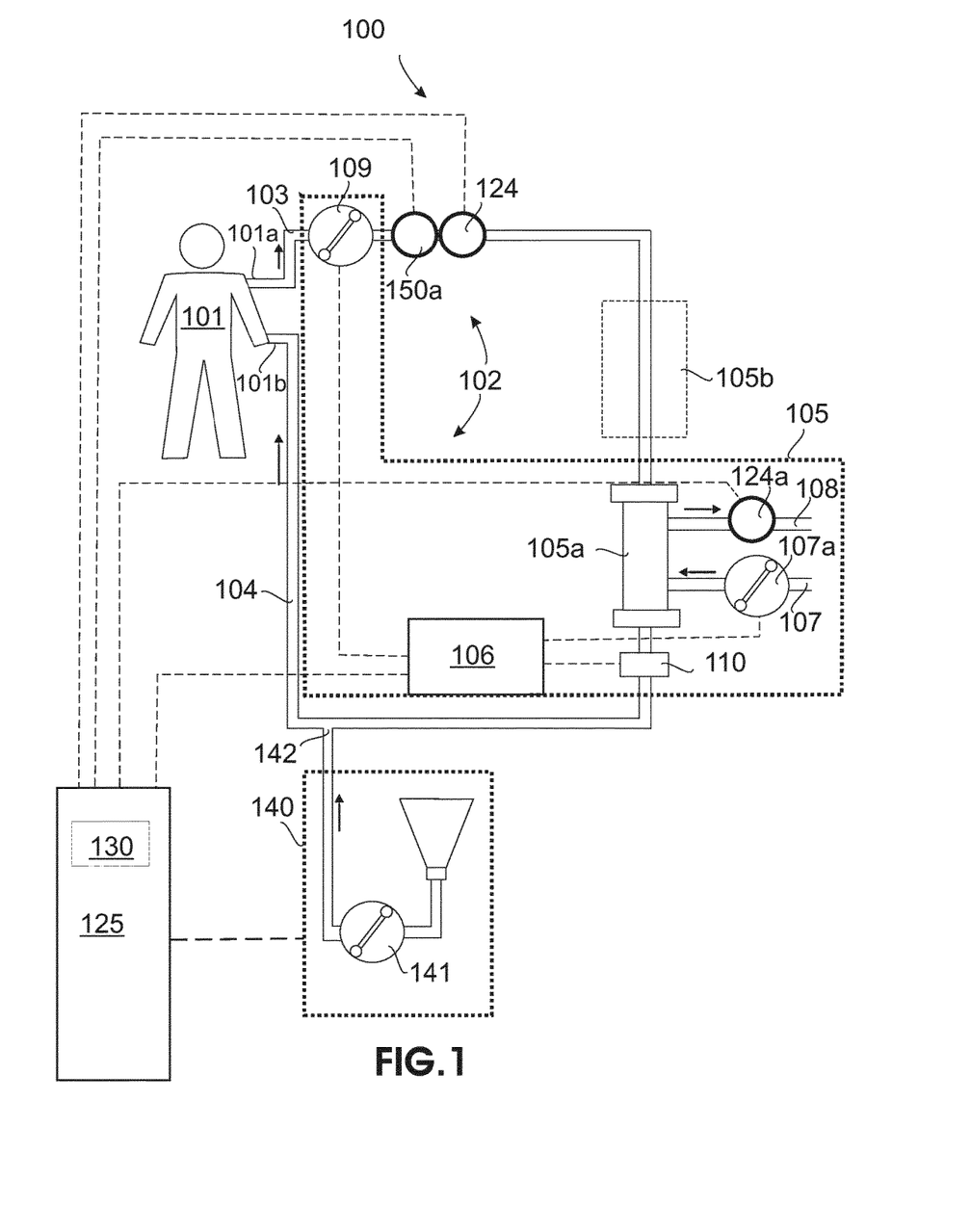
Figure 2:
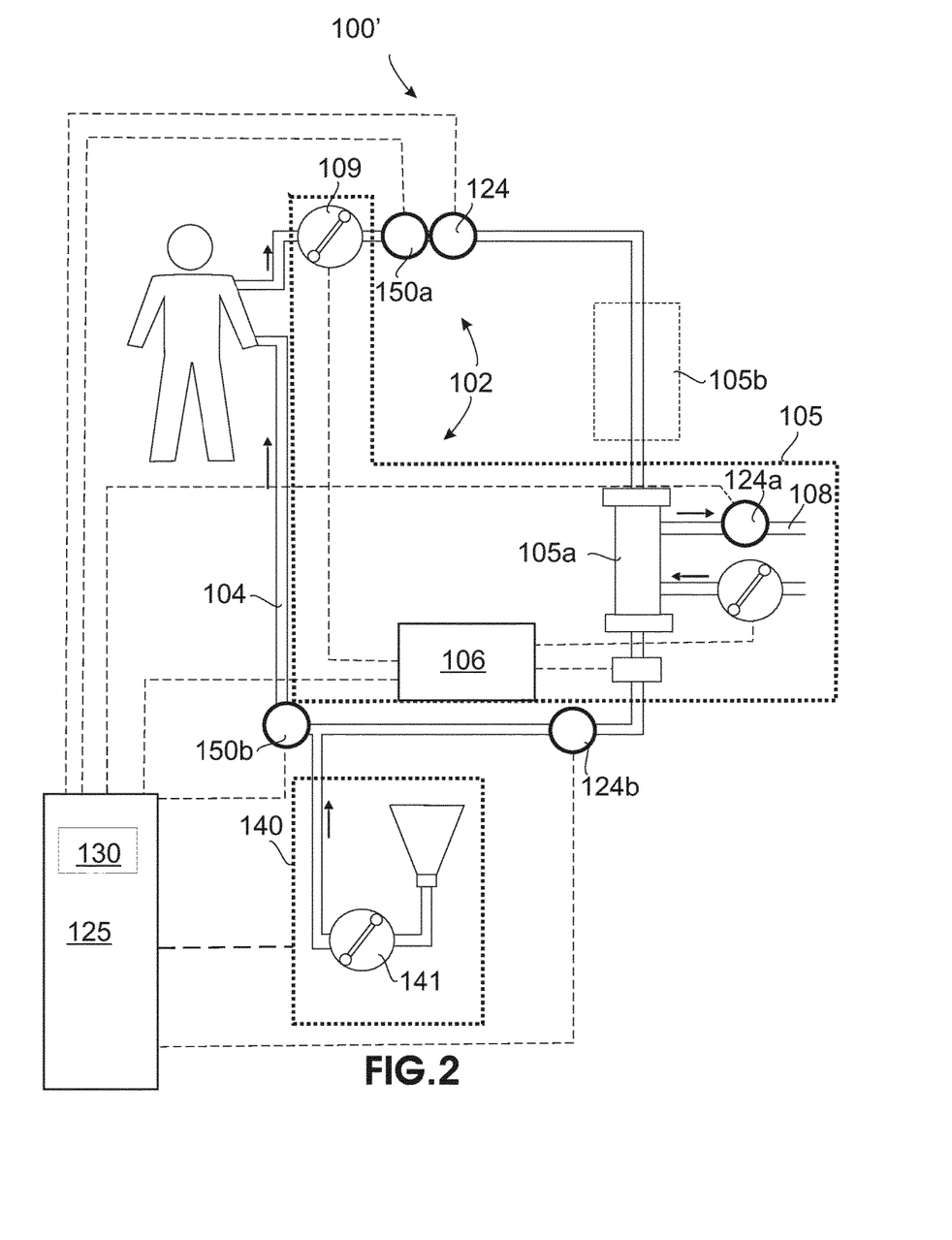
Figure 3:
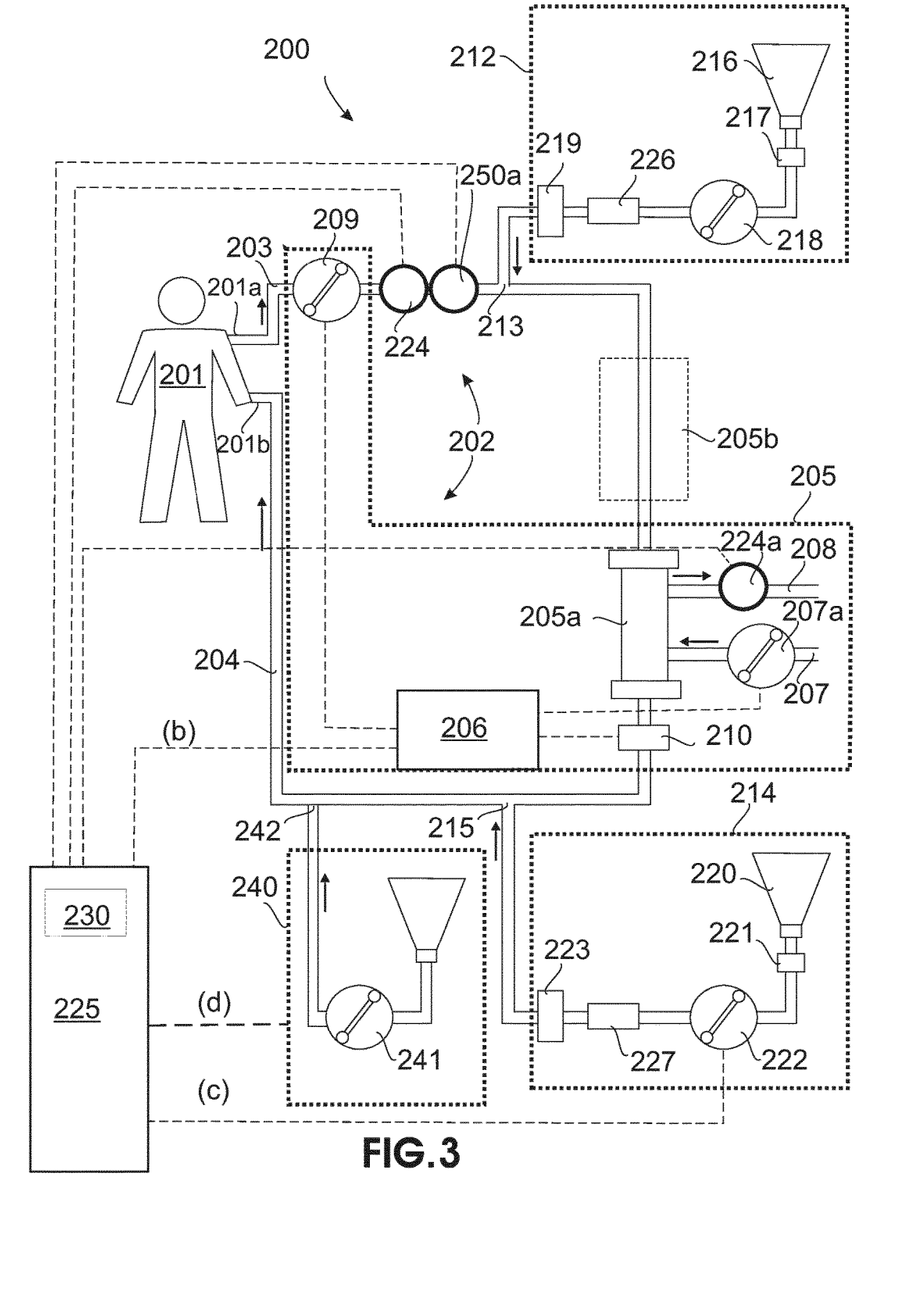
Figure 4:
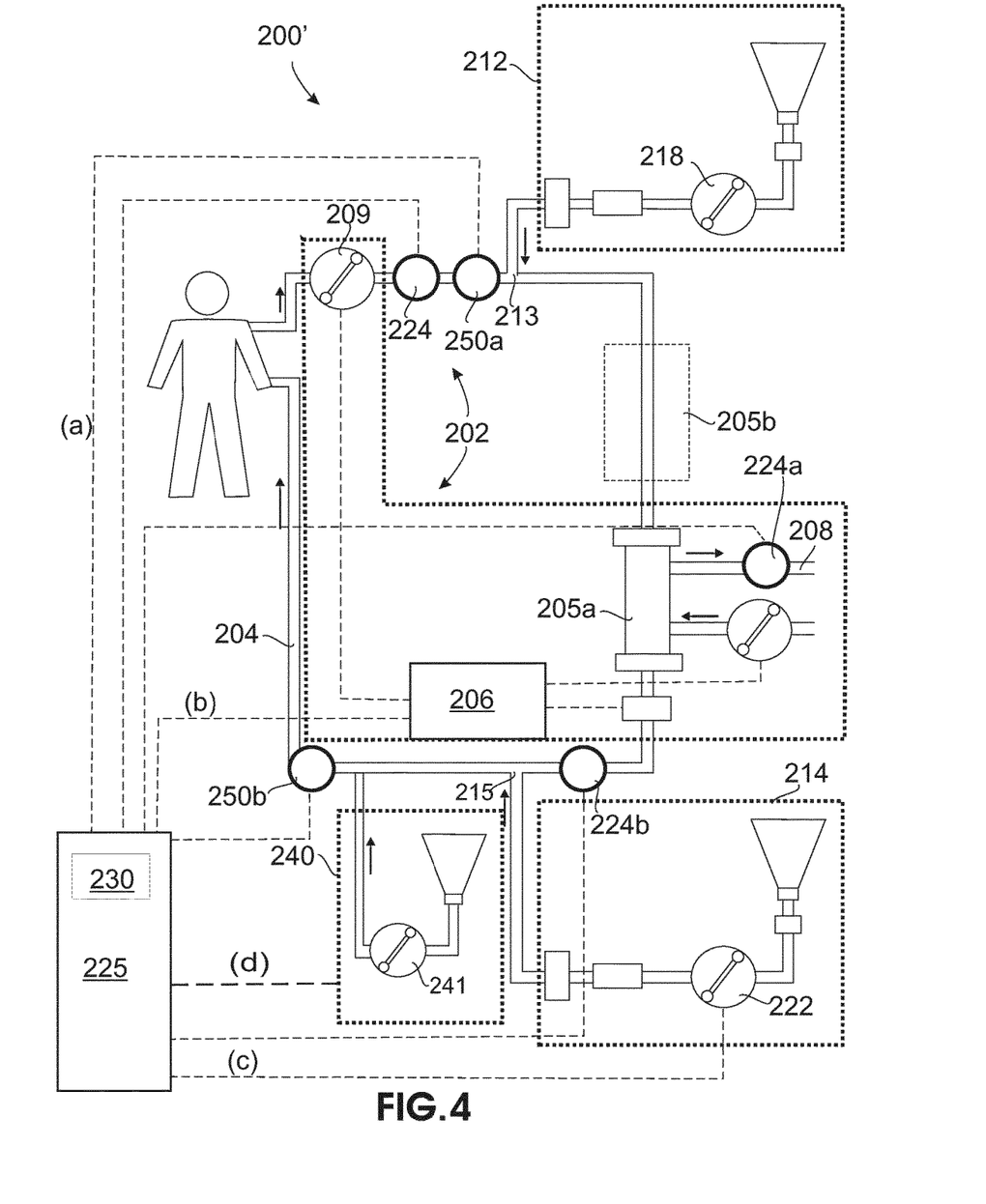

Many embodiments of the invention including further preferences will be explained in greater detail hereinafter on the basis of drawings with non-limiting exemplary embodiments:

In the drawings:

FIG. 1 shows a schematic illustration of a blood purification device according to an embodiment of the invention without citrate anticoagulation, FIG. 2 shows variants of the blood purification device shown in FIG. 1 with additional components, FIG. 3 shows a schematic illustration of a blood purification device according to an embodiment of the invention with citrate anticoagulation, and FIG. 4 shows variants of the blood purification device shown in FIG. 3 with additional components.

The signal connections between the individual device components or to the controllers, control apparatuses and alarm apparatuses are symbolised in the figures by dashed lines.

FIG. 1 shows a schematic illustration of a blood purification device 100 according to an embodiment of the invention without citrate anticoagulation apparatus. Here, the anticoagulation is performed by way of example using Heparin. The blood of the patient 101 reaches the extracorporeal blood circuit 102 via an arterial access 101a, said blood circuit having a blood inflow 103 (arterial branch), a blood outflow 104 (venous branch) and a dialysis unit 105 arranged therebetween (illustrated by a dashed border), and flows via a venous access 101b back into the patient 101. The dialysis unit 105 is composed basically of a dialysis filter 105a (also referred to as dialyser 105a), a blood pump 109, a bubble trap with air bubble detector 110 and a controller 106. Depending on the blood purification system and necessary treatment, an additional blood purification element 105b (for example a haemofilter, a haemofilter with closed plasma circuit or an absorber circuit) can also be provided upstream of the dialysis filter 105a. In the dialysis filter 105a, the blood is combined with the dialysis solution via a semi-permeable membrane. The dialysis solution is usually produced by the dialysis unit by diluting one or more concentrates with water. In this example, the dialysis solution is mixed together from a concentrated acidic component (for example acetate solution) and a concentrated alkaline component (solution containing bicarbonate), further components typical for dialysis solutions, and water (mixing device not shown). By increasing or reducing the supply of bicarbonate solution, the concentration of bicarbonate in the dialysis solution can be varied accordingly. The dialysis solution is pumped by means of a dialysate pump 107a into the dialysis filter 105a via a dialysis solution inflow 107 and is diverted via a dialysate outflow 108 and is disposed of after passing through the dialysis filter 105a. The blood coming from the patient is pumped by means of the blood pump 109 through the extracorporeal blood circuit 102, wherein the rate of the blood flow $Q_B$ is set via the blood pump 109. The blood flow $Q_B$ [ml/min] represents the blood volume that is pumped by the pump per unit of time. In the case of haemodialysis, the blood flow $Q_B$=50-400 ml/min is typically set. Before the blood passes back into the patient 101, it also passes through a bubble trap with air bubble detector 110 for preventing an air embolism. The above-described components form a typical embodiment of an extracorporeal blood purification system.

In accordance with some embodiments of the invention, a control loop for controlling the acid-base balance of the blood is associated with the blood purification device 100. A measuring means for measuring a blood buffer parameter (bicarbonate sensor) is associated with the control loop for this purpose.

In a first embodiment shown in FIG. 1, a bicarbonate sensor 124 ($HCO_3^-$ sensor 124) is arranged upstream of the dialysis filter 105a in the blood circuit 103 of the extracorporeal blood circuit 102 and measures the bicarbonate concentration of the blood. Here, it is irrelevant if the bicarbonate sensor 124 is arranged upstream or downstream of the blood pump 109.

Alternatively to the first embodiment, the bicarbonate sensor can be arranged in a second embodiment in the dialysate outflow 108 (bicarbonate sensor 124a).

The measurements of the bicarbonate concentration are performed at regular intervals, wherein the interval is selected such that a trend in the direction of an unphysiological state (acidosis, alkalosis) of the patient is identified in good time. With most applications, an interval from 30 to 60 minutes is sufficient. With certain patient groups, the interval between two successive measurements is selected so as to be shorter, for example 15 minutes.

For the control and maintenance of the acid-base balance of the blood, a simple control mechanism is created. The bicarbonate sensor 124 or 124a is connected to a control apparatus 125 by means of signal connection. The actual value measured by the bicarbonate sensor 124 or 124a is supplied as a signal corresponding to the bicarbonate concentration of the blood to the control apparatus 125, which regulates the actual value of the blood buffer parameter to a predeterminable intended value or intended range via the supply of bicarbonate. As described above, if bicarbonate is supplied in order to remedy, over the course of the dialysis, the acidosis usually prevailing in dialysis patients or in order to keep constant the acid-base balance during the dialysis in a desirable, very narrow physiological range. Two possibilities for controlling the bicarbonate supply are shown in FIG. 1:

\*) with the first control possibility, the bicarbonate is supplied to the blood by means of the dialysis solution and constitutes a preferred embodiment in the case of haemodialysis and haemodiafiltration. The bicarbonate concentration in the dialysis fluid is therefore increased or reduced accordingly in accordance with the measured actual value by the bicarbonate sensor 124 or 124a. The control apparatus 125 is connected for this purpose to the controller 106 of the dialysis unit 105 via a signal connection. If the measured bicarbonate concentration in the blood falls below the predeterminable intended range, which for example is predetermined as 21-26 mmol/l, an overacidification (acidosis) is then present, and the concentration of the bicarbonate in the dialysis solution is increased by admixing more concentrated alkaline component when mixing together the dialysis solution. In the case of alkalosis, that is to say when the measured bicarbonate concentration in the blood exceeds the intended range, less or even no concentrated alkaline component is admixed accordingly, whereby the bicarbonate concentration in the dialysis solution decreases.

\*) a second possibility for controlling the bicarbonate feed, which is used in particular in the case of haemofiltration and haemodiafiltration, is a separate infusion of an aqueous bicarbonate substitution solution by means of a bicarbonate dosing apparatus 140, wherein the control apparatus 125 activates the bicarbonate pump 141 and varies the dosing of the bicarbonate in accordance with the actual value measured by the bicarbonate sensor 124 or 124a. As is shown in FIG. 1, the aqueous bicarbonate solution is infused into the blood outflow 104 at a bicarbonate supply point 142 downstream of the dialysis filter 105a. By way of example, in the case of "online haemofiltration", a bicarbonate-containing substitution solution is prepared from the dialysate and is supplied in a sterile manner to the patient by means of infusion into the extracorporeal blood circuit.

It is also possible in principle to supply the aqueous bicarbonate solution to the patient 101 via a venous access (not shown), however this option is less preferred, since an additional venous access is provided at the patient.

It is also possible to combine with one another the previously described two possibilities, for example by setting a lower bicarbonate concentration in the dialysate and by a controlled addition via the supply of the substitution solution.

In accordance with several embodiments of the invention, a pH sensor 150a is also arranged upstream of the dialysis filter 105a. The pH value measured at this position thus corresponds to the pH value of the blood present intracorporeally. The pH sensor constitutes an important safety apparatus and makes it possible to distinguish between a compensated and a non-compensated alkalosis or acidosis and also makes it possible to quickly identify life-threatening disturbances of the acid-base balance. The pH sensor 150a is connected to an alarm apparatus 130, associated with the control apparatus 125, via signal connections. If a predeterminable pH value or pH-value range is exceeded or undershot, an alarm signal is triggered by the alarm apparatus 130 and makes an operator, for example a doctor, aware of the state of a non-compensated alkalosis or a non-compensated acidosis. The alarm signal may be an acoustic or optical signal, for example. The alarm may also cause a discontinuation of the entire blood purification device by switch-off of the pumps 109 and 141.

In each of FIGS. 1 to 4, only one bicarbonate sensor or pH sensor is arranged at a certain position in the blood purification device. However, a number of similar sensors, which operate alternately or simultaneously, can also be located at each position.

Instead of the bicarbonate sensors shown in FIGS. 1 to 4, sensors for measuring the $CO_2$ partial pressure ($pCO_2$ sensors) can also be used. Bicarbonate sensors or sensors for measuring the $CO_2$ partial pressure, as are presented in the application and as are shown in the shown examples in FIGS. 1 to 4, are disclosed for example in EP 0759 551 B1, CA 2173672 A2 and US 2009/027095 A1.

FIG. 2 shows variants of the blood purification device 100 shown in FIG. 1 with additional components. The device 100' shown in FIG. 2 corresponds to that in FIG. 1, unless otherwise specified hereinafter. The illustrated additions can be used individually or in combination.

As a development of the above-mentioned embodiment, in which at least one first bicarbonate sensor is arranged in a first position, at least one additional bicarbonate sensor can be associated as a further safety measure with the control loop at one or more further positions. The additional bicarbonate sensor at one or more further positions is used either to identify malfunctions of the first bicarbonate sensor functioning for control or can also be incorporated into the control, as described above, similarly to the bicarbonate sensor at the first position.

In a first variant shown in FIG. 2, with the presence of a bicarbonate sensor 124 upstream of the dialysis filter, a bicarbonate sensor 124a arranged in the dialysate outflow 108 is associated with the control loop upstream of the dialysis filter. Alternatively, in a second variant, with presence of a bicarbonate sensor 124a in the dialysate outflow 108, a bicarbonate sensor 124 is associated with the control loop in the extracorporeal blood circuit 102 upstream of the dialysis unit 105a.

In a further aspect, an additional bicarbonate sensor 124b can be arranged downstream of the dialysis unit 105a. At this position in the extracorporeal blood circuit 102, an acid-base equilibrium lying the in the physiological range should be provided again.

In a further aspect, a further pH sensor 150b is arranged in the blood outflow 104 downstream of the dialysis filter 105a additionally to the pH sensor 150a when bicarbonate is supplied via the dialysis fluid. If the bicarbonate is supplied via a substitution solution, the pH sensor is thus expediently arranged in the blood outflow 104 downstream of the bicarbonate supply point 142. This enables a control of the pH value of the blood in the extracorporeal blood circuit shortly before the blood re-enters the patient. By way of example, incorrect dosings of bicarbonate in the dialysis fluid or in the substitution fluid can be quickly identified.

Similarly to the pH sensor 150a, the pH sensor 150b is also connected via signal connections to an alarm apparatus 130 associated with the control apparatus 125. If a predeterminable pH value or pH-value range is exceeded or undershot, an alarm signal is triggered by the alarm apparatus 130 and makes an operator, for example a doctor, aware of the state of a non-compensated alkalosis or a non-compensated acidosis. The alarm signal may be an acoustic or optical signal, for example. The alarm may also cause a discontinuation of the entire blood purification device by switch-off of the pumps 109 and 141.

FIG. 3 shows a schematic illustration of a blood purification device 200 according to an embodiment of the invention with automated citrate anticoagulation. The blood of the patient 201 passes via an arterial access 201a into the extracorporeal blood circuit 202 comprising a blood inflow 203 (arterial branch), a blood outflow 204 (venous branch) and an intermediate dialysis unit 205 (illustrated by a dashed border) and flows back into the patient via a venous access 201b. The dialysis unit 205 is composed basically of a dialysis filter 205a, a blood pump 209, a bubble trap with air bubble detector 210 and a controller 206. Depending on the blood purification system and necessary treatment, an additional blood purification element 205b (for example a haemofilter, a haemofilter with closed plasma circuit or an absorber circuit) can also be provided upstream of the dialysis filter 205a. The blood is combined with the dialysis solution in the dialysis filter 205a via a semi-permeable membrane. The dialysis solution is usually produced by the dialysis device by diluting one or more concentrates with water. In this example, the dialysis solution can be mixed together from a concentrated acidic component (for example acetate solution) and a concentrated alkaline component (solution containing bicarbonate), further components typical for dialysis solutions and water (mixing device not shown). By increasing or reducing the supply of bicarbonate solution, the concentration of the bicarbonate in the dialysis solution can vary accordingly. The dialysis solution is pumped into the dialysis filter 205a via a dialysis solution inflow 207 by means of a dialysate pump 207a and is diverted via a dialysate outflow 208 and is disposed of after passing through the dialysis filter 205a. The blood coming from the patient is pumped through the extracorporeal blood circuit 202 by means of the blood pump 209, wherein the rate of the blood flow $Q_B$ is set via the blood pump 209. The blood flow $Q_B$ [ml/min] represents the blood volume that is pumped by the pump per unit of time. In the case of haemodialysis, a blood flow $Q_B$=50-400 ml/min is typically set. Before the blood re-enters the patient 201, it also passes a bubble trap with air bubble detector 210 for preventing an air embolism. The above-described components form a typical embodiment of an extracorporeal blood purification system.

The blood purification device 200 further comprises a device for citrate anticoagulation with a controlled citrate dosing apparatus 212 for supplying citrate at a citrate supply point 213 upstream of the dialysis filter 205a (and of the blood purification element 205b when provided) and with a controlled substitution medium dosing apparatus 214 for supplying a substitution medium at a substitution medium supply point 215 downstream of the dialysis filter 205a. The citrate dosing apparatus 212 comprises a container containing citrate solution 216, a drop detector 217, a citrate pump 218, a pressure sensor 226 and an air bubble detector 219. The coagulation of the blood is inhibited due to the infusion of the citrate solution, which, besides citrate, also contains citric acid and dextrose either in the form of $Na_3$ citrate or ACD-A (acid citrate dextrose-A), at the citrate supply point 213 into the extracorporeal blood circuit 202. Similarly to the citrate dosing apparatus 212, the substitution medium dosing apparatus 214 also includes a container containing substitution medium 220, a drop detector 221, a substitution medium pump 222, a pressure sensor 227 and an air bubble detector 223. The substitution medium contains predominantly Ca ions or Ca or Mg ions and is infused into the extracorporeal blood circuit 202 at the substitution medium supply point 215. The rotation speed of the pumps 218, 222 is determined and monitored using Hall sensors integrated in the pumps 218, 222 and incremental meter readers.

In accordance with many embodiments of the invention, a control loop for controlling the acid-base balance of the blood is associated with the blood purification device 200. For this purpose, a measuring means for measuring a blood buffer parameter (bicarbonate sensor) is associated with the control loop.

In a first embodiment shown in FIG. 3, a bicarbonate sensor 224 ($HCO_3^-$ sensor 224) is arranged in the blood inflow 203 of the extracorporeal blood circuit 202 upstream of the citrate supply point 213 and measures the bicarbonate concentration of the blood. Here, it is irrelevant whether the bicarbonate sensor 224 is arranged downstream or upstream of the blood pump 209.

Alternatively to the first embodiment, the bicarbonate sensor can be arranged in a second embodiment in the dialysate outflow 208 (bicarbonate sensor 224a).

The measurements of the bicarbonate concentration are performed at regular intervals wherein the interval is selected such that a trend in the direction of the unphysiological state (acidosis, alkalosis) of the patient is identified in good time. In most applications, an interval from 30 to 60 minutes is sufficient. With certain patient groups, for example patients with liver diseases, who can only convert the supplied citrate into bicarbonate to a limited extent, the interval between two successive measurements is selected so as to be shorter, for example 15 minutes.

For the control and maintenance of the acid-base balance of the blood, a simple control mechanism is created. The bicarbonate sensor 224 or 224a is connected by means of signal connection to a control apparatus 225. The actual value measured by the bicarbonate sensor 224 or 224a is supplied as a signal corresponding to the bicarbonate concentration of the blood to the control apparatus 225, which regulates the actual value of the blood buffer parameter via the supply of bicarbonate to a predeterminable intended value or intended range. As described above, bicarbonate is supplied in order to remedy, over the course of the dialysis, the acidosis usually prevailing in dialysis patients or to keep constant the acid-base balance during the dialysis in a desirable, very narrow physiological range. Three possibilities for controlling the bicarbonate supply are shown in FIG. 3:

*) with the first control possibility, the bicarbonate is supplied to the blood by means of the dialysis solution. The first control possibility constitutes a preferred embodiment in the case of haemodialysis and haemodiafiltration. The bicarbonate concentration in the dialysis fluid is therefore increased or reduced accordingly in accordance with the measured actual value by the bicarbonate sensor 224 or 224*a*. The control apparatus 225 is connected to the controller 206 of the dialysis unit 205 for this purpose. If the measured bicarbonate concentration in the blood falls below the predeterminable intended range, which for example is predetermined as 21-26 mmol/l, an overacidification (acidosis) is then present and the concentration of the bicarbonate in the dialysis solution is increased by admixing more concentrated alkaline component when mixing together the dialysis solution. In the case of alkalosis, that is to say when the measured bicarbonate concentration in the blood exceeds the intended range, less or even no concentrated alkaline component is admixed accordingly, whereby the bicarbonate concentration in the dialysis solution decreases.

*) with the second control possibility, the bicarbonate is supplied by means of the substitution medium to the citrate anticoagulation apparatus, which also contains bicarbonate in addition to the other ions, such as calcium ions or magnesium ions. The control apparatus 225 controls the bicarbonate supply in accordance with the bicarbonate concentration measured by the bicarbonate sensor 224 or 224*a* and therefore controls the acid-base balance by activating the substitution medium pump 222 of the substitution medium dosing apparatus 214. This possibility is less preferred, since not only is the bicarbonate supply modified by changing the supply of the substitution medium, but also the supply of the other important ions (calcium and magnesium ions), which may lead in some cases to physiological imbalances in the electrolyte equilibrium (for example hypocalcaemia and hypercalcaemia).

*) a third possibility for controlling the bicarbonate supply, which is used in particular in the case of haemofiltration and haemodiafiltration, is a separate infusion of an aqueous bicarbonate substitution solution by means of a bicarbonate dosing apparatus 240, wherein the controller 225 activates the bicarbonate pump 241 and varies the dosing of the bicarbonate in accordance with the actual value measured by the bicarbonate sensor 224. The disadvantages of the second possibility (precipitation of calcium carbonate and magnesium carbonate) can thus be bypassed. As is shown in FIG. 3, the aqueous bicarbonate solution is infused into the blood outflow 204 at a bicarbonate supply point 242. In the case of "online haemofiltration", a substitution solution for example is prepared from the dialysate and is supplied in a sterile manner to the patient by infusion into the extracorporeal blood circuit.

It is also possible in principle to supply the aqueous bicarbonate solution to the patient 201 via a venous access (not shown), however this option is less preferred.

It is also possible to combine with one another the previously described three possibilities, for example by setting a lower bicarbonate concentration in the dialysate and by a controlled addition via the substitution medium.

In accordance with several embodiments of the invention, a pH sensor 250*a* is also arranged in the blood inflow 203 upstream of the citrate supply 213. The pH value measured at this position thus corresponds to the pH value of the blood present intracorporeally. The pH sensor constitutes a key safety apparatus and makes it possible to distinguish between a compensated and a non-compensated alkalosis or acidosis and makes it possible to quickly identify life-threatening disturbances of the acid-base balance. The pH sensor 250*a* is connected via signal connections to an alarm apparatus 230 associated with the control apparatus 225. If a predeterminable pH value or pH-value range is exceeded or undershot, an alarm signal is triggered by the alarm apparatus 230 and makes an operator, for example a doctor, aware of the state of a non-compensated alkalosis or a non-compensated acidosis. The alarm signal may be an acoustic or optical signal, for example. The alarm may also cause a discontinuation of the entire blood purification device by switch-off of the pumps 209, 218, 222 and 241.

FIG. 4 shows variants of the blood purification device 200 shown in FIG. 3 with additional components. The device 200' shown in FIG. 4 corresponds to that of FIG. 3 unless specified otherwise hereinafter. The presented additions can be used individually or in combination.

As a development of the embodiment shown in FIG. 3 and variants in which at least one first bicarbonate sensor is arranged in a first position, at least one additional bicarbonate sensor can be associated as a further safety measure with the control loop at one or more further positions. The additional bicarbonate sensor at one or more further positions is used either to identify malfunctions of the first bicarbonate sensor functioning for control or, similarly to the bicarbonate sensor at the first position, can also be included in the control as prescribed above.

In a first variant shown in FIG. 4, with the presence of a bicarbonate sensor 224 upstream of the citrate supply point 213, a bicarbonate sensor 224*a* arranged in the dialysate outflow 208 is associated with the control loop. Alternatively, in a second variant with the presence of bicarbonate sensor 224*a* in the dialysate outflow 208, a bicarbonate sensor 224 is associated with the control loop in the extracorporeal blood circuit 202 upstream of the citrate supply point 213.

In a further aspect, an additional bicarbonate sensor 224*b* can be arranged downstream of the dialysis unit 205*a* and upstream of the substitution medium supply point 215. An acid-base equilibrium lying in the physiological range should be present again at this position in the extracorporeal blood circuit 202.

In a further aspect, a further pH sensor 250*b* is arranged in the blood outflow 204 in addition to the pH sensor 250*a* when bicarbonate is supplied via the dialysis fluid. If the bicarbonate is supplied via substitution solution, the pH sensor is expediently arranged in the blood outflow 204 downstream of the substitution medium supply point 215 or the bicarbonate supply point 142 following addition of bicarbonate. This makes it possible to check the pH value of the blood in the extracorporeal blood circuit shortly before the blood re-enters the patient. For example, incorrect dosings of the bicarbonate and/or the citrate in the dialysis fluid, the citrate solution and in the substitution fluids can be quickly identified.

Similarly to the pH sensor 250*a*, the pH sensor 250*b* is also connected via signal connections to an alarm apparatus 230 associated with the control apparatus 125. If a predeterminable pH value or pH-value range is exceeded or undershot, an alarm signal is triggered by the alarm apparatus 230 and makes an operator, for example a doctor, aware of the state of a non-compensated alkalosis or a non-compensated acidosis. The alarm signal may be an acoustic or optical signal, for example. The alarm may also cause a discontinuation of the entire blood purification device by switch-off of the pumps 209, 218, 222 and 241.

The above-described implementations are only examples of many options and consequently are not to be considered as limiting.

The invention claimed is:

1. A blood purification device comprising:
an extracorporeal blood circuit with a blood inflow to a dialysis unit for blood removed from a patient and a blood outflow from the dialysis unit for blood being guided back into the patient, wherein the dialysis unit comprises an inflow for a dialysis solution and a dialysate outflow,
a citrate anticoagulation apparatus, wherein citrate is supplied to the extracorporeal blood circuit at a citrate supply point upstream of the dialysis unit and a substitute medium dosing apparatus, wherein substitution medium is supplied at a substitution medium supply point downstream of the dialysis unit,
a control loop for controlling the acid-base balance of the blood, wherein bicarbonate is supplied to the blood by means of an aqueous bicarbonate-containing solution, wherein at least one measuring means for measuring a blood buffer parameter is associated with the control loop and upstream of the citrate supply point in the extracorporeal blood circuit, wherein the blood buffer parameter is selected from the group consisting of bicarbonate concentration and $CO_2$ partial pressure, and wherein a signal corresponding to the measured actual value of the blood buffer parameter can be supplied to a control apparatus, which regulates the actual value of the blood buffer parameter via the supply of bicarbonate to a predeterminable intended value or intended value range,
at least one pH-measuring means, which is arranged upstream of the citrate supply point in the extracorporeal blood circuit, wherein a signal corresponding to the pH value can be supplied to an alarm apparatus, which triggers an alarm signal if a predeterminable pH value or a pH-value range is exceeded or undershot,
wherein the arrangement of the at least one measuring means for measuring a blood buffer parameter located upstream of the citrate supply point in the extracorporeal blood circuit and the at least one pH-measuring arranged upstream of the citrate supply point are configured to detect and prevent or treat disturbances of the acid-base balance during an extracorporeal blood purification selected from the group of compensated acidosis, non-compensated acidosis, compensated alkalosis and compensated or non-compensated alkalosis,
at least one additional measuring means for measuring a blood buffer parameter that is associated with the control loop and arranged downstream of the dialysis unit and upstream of the substitution medium supply point in the extracorporeal blood circuit, and
at least one additional pH-measuring means that is arranged downstream of the substitution medium supply point in the extracorporeal blood circuit, wherein a signal corresponding to the pH value can be supplied to the alarm apparatus, which triggers an alarm signal if a predeterminable pH value or pH-value range is exceeded or undershot.

2. The blood purification device according to claim 1, wherein the aqueous bicarbonate-containing solution is a dialysis solution.

3. The blood purification device according to claim 1, wherein the aqueous bicarbonate-containing solution is an infusion solution.

4. The blood purification device according to claim 1, wherein at least one additional measuring means for measuring a blood buffer parameter is comprised within the control loop and is arranged upstream of the dialysis unit in the extracorporeal blood circuit.

5. The blood purification device according to claim 1, wherein at least one additional measuring means for measuring a blood buffer parameter is comprised within the control loop and is arranged upstream of the citrate supply point in the extracorporeal blood circuit.

6. The blood purification device according to claim 1, wherein at least one additional measuring means for measuring a blood buffer parameter is associated with the control loop and is arranged in the dialysate outflow.

* * * * *